APPARATUS FOR OBSERVING VOCAL CORD WAVE

Original Filed March 3, 1964

INVENTORS
TANETOSHI MIURA
TSUNEJI KOSHIKAWA

BY Paul M. Craig, Jr.
ATTORNEY

United States Patent Office

Re. 26,600
Reissued June 3, 1969

26,600
APPARATUS FOR OBSERVING VOCAL CORD WAVE

Tanetoshi Miura and Tsuneji Koshikawa, by Hitachi, Ltd., Tokyo, Japan, a corporation of Japan, assignee Original No. 3,345,979, dated Oct. 10, 1967, Ser. No. 349,059, Mar. 3, 1964. Application for reissue Dec. 13, 1967, Ser. No. 698,065
Claims priority, application Japan, Apr. 3, 1963, 38/16,372
Int. Cl. A61b *5/10*
U.S. Cl. 128—2 4 Claims

Matter enclosed in heavy brackets [ ] appears in the original patent but forms no part of this reissue specification; matter printed in italics indicates the additions made by reissue.

This invention relates to an apparatus for observing the wave form and pitch fluctuation features of vocal cord waves.

Vocal cord waves have an important role in linguistic education, vocal training and medical diagnosis in which defective functioning of vocalization is to be detected and an appropriate treatment for vocal disorder is to be determined. In order to judge the functioning of vocalization accurately it is particularly important to know the wave form and pitch fluctuation features of the vocal waves.

It is an object of the present invention to provide an apparatus for observing quantitatively and objectively the wave form and pitch fluctuation features of vocal waves and thereby provide significant insights for the functioning of vocalization.

Figure 1:
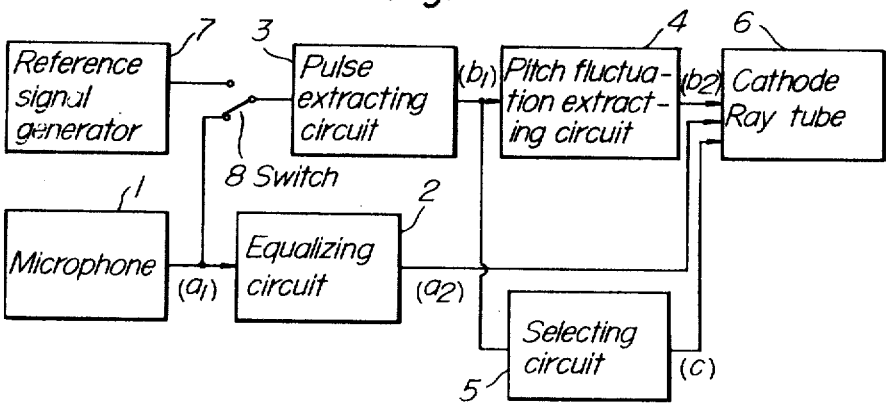
Figure 1:
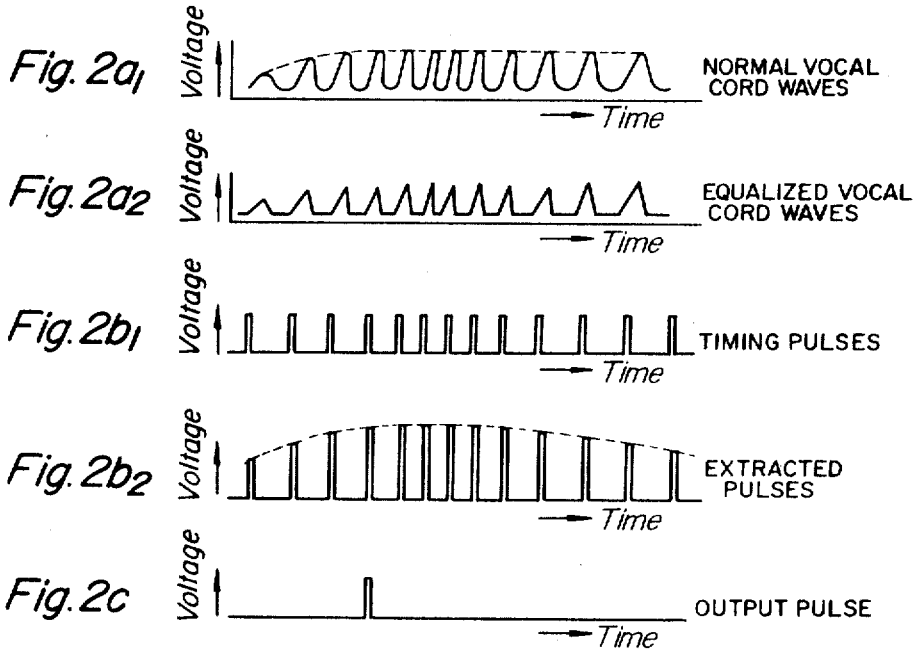

The present invention will now be described in detail with reference to the accompanying drawings which illustrate an embodiment thereof and in which:

FIGURE 1 shows a block diagram of an apparatus embodying the present invention, and FIGURES 2*a* to 2*c* show wave forms which are used to explain the operation of the apparatus illustrated in block diagram form in FIGURE 1.

Referring to FIGURE 1, numeral 1 represents a microphone for extracting body wall vibrations at the trachea and for translating the vibrations into electrical waves. The microphone 1 which is of the type described in an article entitled, "On the Extraction of the Pitch Signal Using the Body Wall Vibration at the Throat of the Talker," by Toshikako Sugimoto and Shizuo Hiki appearing in the proceedings of the Fourth International Congress of Acoustics held at Copenhagen on Aug. 21–28, 1962, pages 1 through 4—paper number G26, is held pressed against the wall of the trachea at a predetermined location. An equalizing circuit 2 is connected to the microphone 1 to compensate for loss characteristics introduced by the wall of the trachea to the vocal cord waves. These losses are approximated by a low pass filtering characteristic and are compensated for by a filter built into equalizing circuit 2. Suitable filters for this purpose are disclosed in the Electrical Engineers Handbook, published by John Wiley & Sons, Inc., fourth edition, fourth printing, February 1963 and appearing on pages 6–54, 6–55 thereof. The body wall vibrations at the trachea (having a wave form shown in FIGURE $2a_1$) are extracted by the microphone 1 and transformed into a (wave form shown in FIGURE $2a_2$) are similar to the vocal cord waves by passing through the equalizing circuit 2.

A circuit 3 also is connected to the microphone 1 through a switch 8 to a timing pulse extracting circuit 3 which may be of the type described in the paper entitled "Extraction and Portrayal of Pitch of Speech Sounds"—O. O. Gruenz, Jr. and L. O. Schott appearing in volume 21, number 5 of the Journal of the Acoustical Society of America, September 1949, pages 487 through 495. The timing pulse extracting circuit 3 serves to extract a series of timing pulses (shown in FIGURE $2b_1$) having a period which is equal to the fundamental period of the related vocal cord waves. A pitch fluctuation extracting circuit 4, which may be of the type described in the periodical "Electrical Communication" a technical journal published by the International Telephone and Telegraph Corporation—volume 23, number 2, published June 1946 and appearing on pages 165 through 171 thereof. The pitch fluctuation extracting circuit 4 is connected to the circuit 3 to transform successive lengths of the period (time intervals between succeeding pulses) of said series of pulses into a series of varying pulses. The extracting circuit 4 includes amplifying or level shifting circuit for adjusting the voltage value of the pulses about a median value. The output of the extracting circuit 4 is shown in FIGURE $2b_2$.

A counting and selecting circuit 5 also is connected to the output of the circuit 3 and counts the output pulses of the circuit 3 in order to obtain an output synchronized with the arrival of a desired pulse in the series. The output of the counting and selecting circuit 5, which may be of the type described in an article entitled "An Industrial Batching Counter" by R. W. Brierley appearing in Electronic Engineering Magazine—April 1954 issue—pages 157 through 160, is represented by a wave form shown in FIGURE 2*c*. The pitch fluctuation shown in FIGURE $2b_2$ which is the output of the extracting circuit 4 and the vocal cord wave shown in FIGURE $2a_2$ appearing at the output of the equalizing circuit 2, are displayed on a cathode ray tube 6 with starting of the horizontal sweep being triggered by the output pulse 5 of the counting and selecting circuit C. The sweep time of the cathode ray tube 6 is adjusted to display the phenomenon desired to be observed within a particular time range according to the object of the investigation. Thus wave form and pitch fluctuation features of the vocal cord vibrations can be observed very accurately and quantitatively.

It is preferable to employ a cathode ray tube of long persistency to facilitate direct vision. A reference signal generator 7 may be connected, if required, to the circuit 3 by means of a switch 8 producing a timed series of reference pulses in order to compare the observed wave with the reference signal pulses.

Having described one embodiment of an apparatus for observing vocal cord waves constructed in accordance with the invention, it is believed obvious that other modifications and variations of the invention are possible in the light of the above teachings. It is therefore to be understood that changes may be made in the particular embodiment of the invention described which are within the full intended scope of the invention as defined by the appended claims.

What we claim is:

1. An apparatus for observing vocal cord waves comprising: microphone means for extracting electrical vocal cord waves including pitch fluctuation features of vocal cord vibrations from body wall vibrations at the tracea, filter means operatively coupled to the output from said microphone means for compensating for loss characteristics of the wall of the trachea to said vocal cord wave, and time base display means operatively coupled to the output from said filter means for displaying said vocal cord waves including the pitch fluctation features on an expanded time base scale for observation purposes.

2. An apparatus for observing vocal cord waves comprising: microphone means for extracting electrical vocal cord waves from body wall waves at the trachea, filter means operatively coupled to the output from said microphone means for compensating for loss characteristics of the wall of the trachea to said vocal cord waves, first pulse forming circuit means operatively coupled to the output of said filter means for extracting pulses having a period which is equal to the fundamental period of said vocal cord waves, second pulse forming circuit means operatively coupled to the output from said first pulse forming circuit means for transforming successive lengths of period into successive variable voltage pulses to extract pitch fluctuation features, and time base display means operatively coupled to the output of said filter means and said second pulse forming circuit means for displaying said vocal cord waves including the pitch fluctuation features on an expanded time base scale for observation purposes.

3. An apparatus for observing electrical vocal cord waves according to claim 2 further comprising third pulse forming circuit means operatively coupled to the output from said first pulse forming circuit means for deriving a desired synchronizing pulse signal from the output thereof and means for supplying the synchronizing pulse signal to the time base display means for synchronizing the time base scan thereof.

4. An apparatus for observing electrical vocal cord waves according to claim 3 further comprising reference signal generator means and selector switch means for selectively coupling the output from said reference signal generator means to the input of said first pulse forming circuit means in place of the output from said filter means.

References Cited

The following references, cited by the Examiner, are of record in the patented file of this patent or the original patent.

UNITED STATES PATENTS

| | | | |
|---|---|---|---|
| 2,705,742 | 4/1955 | Miller | 179—1 |
| 3,024,783 | 3/1962 | Timcke | 128—2 |

RICHARD A. GAUDET, *Primary Examiner.*

K. L. HOWELL, *Assistant Examiner.*